(12) United States Patent
Judd et al.

(10) Patent No.: US 8,617,122 B2
(45) Date of Patent: Dec. 31, 2013

(54) SYRINGE NEEDLE SHEATH

(75) Inventors: Damien Judd, Coomera Springs (AU);
Joseph Hermes Kaal, Morpeth (AU);
Craig Stephen Thorley, Largs (AU)

(73) Assignee: Unitract Syringe Pty Ltd, Newcastle, New South Wales (AU)

( * ) Notice: Subject to any disclaimer, the term of this patent is extended or adjusted under 35 U.S.C. 154(b) by 123 days.

(21) Appl. No.: 13/084,330

(22) Filed: Apr. 11, 2011

(65) Prior Publication Data
US 2011/0190699 A1    Aug. 4, 2011

Related U.S. Application Data

(62) Division of application No. 11/572,249, filed as application No. PCT/AU2005/001054 on Jul. 18, 2005, now Pat. No. 7,935,087.

(60) Provisional application No. 60/638,504, filed on Dec. 23, 2004.

(30) Foreign Application Priority Data

Jul. 16, 2004   (AU) .............................. 2004903915
May 18, 2005   (AU) .............................. 2005902526

(51) Int. Cl.
*A61M 5/32*     (2006.01)
*A61M 5/00*     (2006.01)

(52) U.S. Cl.
USPC ........................... 604/198; 604/192; 604/187

(58) Field of Classification Search
USPC ......... 604/110, 187, 192, 195, 198, 250, 263, 604/537
See application file for complete search history.

(56) References Cited

U.S. PATENT DOCUMENTS

| 4,846,796 | A |   | 7/1989  | Carrell et al. |         |
|-----------|---|---|---------|----------------|---------|
| 4,863,435 | A |   | 9/1989  | Sturman et al. |         |
| 5,049,133 | A |   | 9/1991  | Villen Pascual |         |
| 5,151,088 | A | * | 9/1992  | Allison et al. ................. | 604/192 |
| 5,360,408 | A | * | 11/1994 | Vaillancourt ................. | 604/198 |
| 5,370,628 | A | * | 12/1994 | Allison et al. ................. | 604/192 |
| 5,658,259 | A | * | 8/1997  | Pearson et al. ................. | 604/232 |
| 5,695,463 | A |   | 12/1997 | Cherif-Cheikh  |         |
| 6,086,566 | A | * | 7/2000  | Arnissolle ..................... | 604/192 |

(Continued)

FOREIGN PATENT DOCUMENTS

EP   1334740 A1   8/2003
WO   WO97/02855   1/1997

(Continued)

*Primary Examiner* — Kevin C Sirmons
*Assistant Examiner* — William Carpenter
(74) *Attorney, Agent, or Firm* — LeClairRyan, A Professional Corporation

(57) ABSTRACT

A syringe is provided which comprises a barrel (11) and a needle sheath (30) slidably located within the barrel, a plunger (20) with a plunger seal (23), a needle, a needle sheath (30) and a sheath seal (50), arranged so that depression of the plunger forces the needle sheath to move into a position where it covers or at least partly encloses the needle after delivery of fluid contents of the syringe. The needle sheath may be manually actuated or may be actuated by decompression of a spring. The syringe may further comprise a plunger disabling means operable to impede, prevent or otherwise hinder withdrawal of the plunger during or following depression of the plunger. The syringe may be a pre-filled syringe or a syringe which is filled by a user.

7 Claims, 16 Drawing Sheets

(56) References Cited

U.S. PATENT DOCUMENTS

| | | |
|---|---|---|
| 6,179,812 B1 | 1/2001 | Botich et al. |
| 6,443,929 B1 * | 9/2002 | Kuracina et al. ............. 604/192 |
| 6,569,115 B1 * | 5/2003 | Barker et al. ................ 604/110 |
| 6,817,989 B2 * | 11/2004 | Svendsen et al. ............ 604/192 |
| 7,101,351 B2 | 9/2006 | Crawford et al. |
| 8,052,654 B2 * | 11/2011 | Kaal et al. .................... 604/209 |
| 2003/0144630 A1 * | 7/2003 | Chang et al. ................. 604/198 |

FOREIGN PATENT DOCUMENTS

| | | |
|---|---|---|
| WO | WO97/14455 | 4/1997 |
| WO | WO98/26824 | 6/1998 |
| WO | WO02/00277 A2 | 1/2002 |
| WO | WO2006/007642 A1 | 1/2006 |

* cited by examiner

SYRINGE NEEDLE SHEATH

CROSS REFERENCE TO OTHER APPLICATIONS

The present application is a Divisional of U.S. patent application Ser. No. 11/572,249, filed 10 Sep. 2007, and claims priority benefits to national stage entry of PCT/AU05/01054, filed 18 Jul. 2005, U.S. Provisional Application 60/638,504, filed 23 Dec. 2004, Australian Application No. 2005902526, filed 18 May 2005, and Australian Application No. 2004903915, filed 16 Jul. 2004, the contents of which are incorporated herein by reference.

FIELD OF THE INVENTION

THIS INVENTION relates to syringes. More particularly, this invention relates to a syringe that comprises a sheath mechanism to prevent or minimize the risk of needlestick injury. This invention also relates to a syringe that comprises a sheath mechanism to prevent or minimize the risk of needlestick injury and a plunger disabling means to impede, prevent or otherwise hinder withdrawal of the plunger during or following depression of the plunger.

BACKGROUND OF THE INVENTION

The practice of sharing syringes without adequate sterilisation between successive users is a major contributor to the transfer of Human Immunodeficiency Virus (HIV) and Hepatitis with subsequent severe repercussions for the sufferer and at a high cost to society for supporting and providing medical attention to sufferers.

In response to this problem, syringes have been developed with the aim of preventing syringe re-use.

A particular problem associated with syringes is needlestick injury to the user.

One solution has been to develop syringes where the needle is permanently retractable into the barrel of the syringe, retraction driven by a compressed spring, as for example described in International Publication WO 01/80930.

Although very effective, retractable syringes are relatively expensive, particularly when required in large quantities for mass immunizations or for distribution to intravenous drug users. This is particularly a problem in third world countries where the incidence of HIV is high, mass immunization programs need to be frequently undertaken and healthcare resources are limited.

There is therefore a need to produce a syringe that automatically prevents or minimizes the risk of syringe re-use and/or needlestick injury and that is relatively inexpensive to produce.

With this need in mind, syringes with non-retractable needles have been developed, wherein a cover or sheath is activated to cover the needle after syringe use.

In this regard, reference is made to U.S. Pat. No. 6,086,566 and U.S. Pat. No. 6,428,519 which describe a movable needle cover. A particular feature of these prior art syringes is that they are relatively complicated, each requiring a guiding member to assist guided movement of the cover over the needle and also to positively retain the movable cover in its protection position over the needle.

Reference is also made to U.S. Pat. No. 6,565,540 which describes a spring actuated, movable needle cover. A disadvantage of this syringe needle cover is that the spring is gradually compressed during plunger depression, which provides an unacceptable "feel" to the syringe user and hence detracts from the commercial attractiveness of the syringe.

SUMMARY OF THE INVENTION

The present invention is therefore broadly directed to syringe needle sheath operable to prevent or minimize the risk of needlestick injury and/or syringe re-use and which overcomes one or more disadvantages of the prior art or at least provides a commercially suitable alternative.

In one broad form, the invention provides a manually-actuated needle sheath.

In another broad form, the invention provides a spring-actuated needle sheath.

In yet another broad form, the invention provides a syringe comprising a needle sheath and a plunger disabling means.

In a first aspect, the invention provides a needle sheath for a syringe having a barrel, plunger and a needle, said needle sheath slidably located within the barrel and said operable to cover or at least partly enclose the needle after delivery of fluid contents of the syringe.

In a second aspect, the invention provides a syringe comprising a barrel and a needle sheath slidably located within the barrel, a plunger and a needle, said needle sheath operable to cover or at least partly enclose the needle after delivery of fluid contents of the syringe.

In one particular embodiment, the syringe comprises a barrel, a needle mounted to the barrel, a plunger, a needle sheath and a sheath seal, arranged so that depression of said plunger urges or forces said sheath seal to bear against said needle sheath and thereby move said needle sheath to cover or at least partly enclose the needle after delivery of fluid contents of the syringe.

In another particular embodiment, the needle sheath mechanism is spring-activated.

In a preferred form of this embodiment, the syringe comprises a barrel, a needle mounted to a needle mount that is fitted to the barrel, a plunger, a needle sheath, an initially compressed spring and a sheath seal, arranged so that depression of said plunger urges or forces said sheath seal to bear against said needle sheath and thereby release said needle sheath from said needle mount and thereby facilitate decompression of said spring to move said needle sheath so as to cover or at least partly enclose the needle after delivery of fluid contents of the syringe.

The syringe may be a prefilled syringe or a syringe that is fillable by plunger withdrawal.

In a particularly preferred form, the syringe further comprises a plunger disabling means.

Suitably, the plunger disabling means is operable to impede, prevent or otherwise hinder withdrawal of the plunger during or following depression of the plunger.

In one particular embodiment, the plunger disabling means comprises one or more clips, ledges, tabs or the like located at a plunger end of said barrel and which are capable of engaging said plunger to thereby impede, prevent or otherwise hinder withdrawal of said plunger during or following depression of said plunger.

In another particular embodiment, the plunger disabling means is essentially as described in International Application PCT/AU2005/000106, which is herein incorporated by reference in its entirety.

In one form of this particular embodiment, the plunger comprises two opposed ratchets disposed along the plunger rod, which ratchets are respectively alignable with two pawls so as to be capable of engagement by the pawls and thereby impede, prevent or otherwise hinder withdrawal of the plunger during or following depression of the plunger. The syringe further comprises a collar at a plunger end of the barrel, the collar having an inner member and an outer member that are incapable of rotation relative to each other. The outer member comprises said two pawls and further comprises two fingers that respectively slidably engage opposed guide slots on the plunger to thereby prevent or minimize rotation of the plunger relative to the collar. The inner member of the collar is operable to prevent engagement of the plunger ratchet by the two pawls until the plunger is depressed.

Throughout this specification, unless otherwise indicated, "comprise", "comprises" and "comprising" are used inclusively rather than exclusively, so that a stated integer or group of integers may include one or more other non-stated integers or groups of integers.

BRIEF DESCRIPTION OF THE DRAWINGS

Non-limiting embodiments of the invention are described herein with reference to drawings wherein.

DETAILED DESCRIPTION OF THE INVENTION

Figure 1:
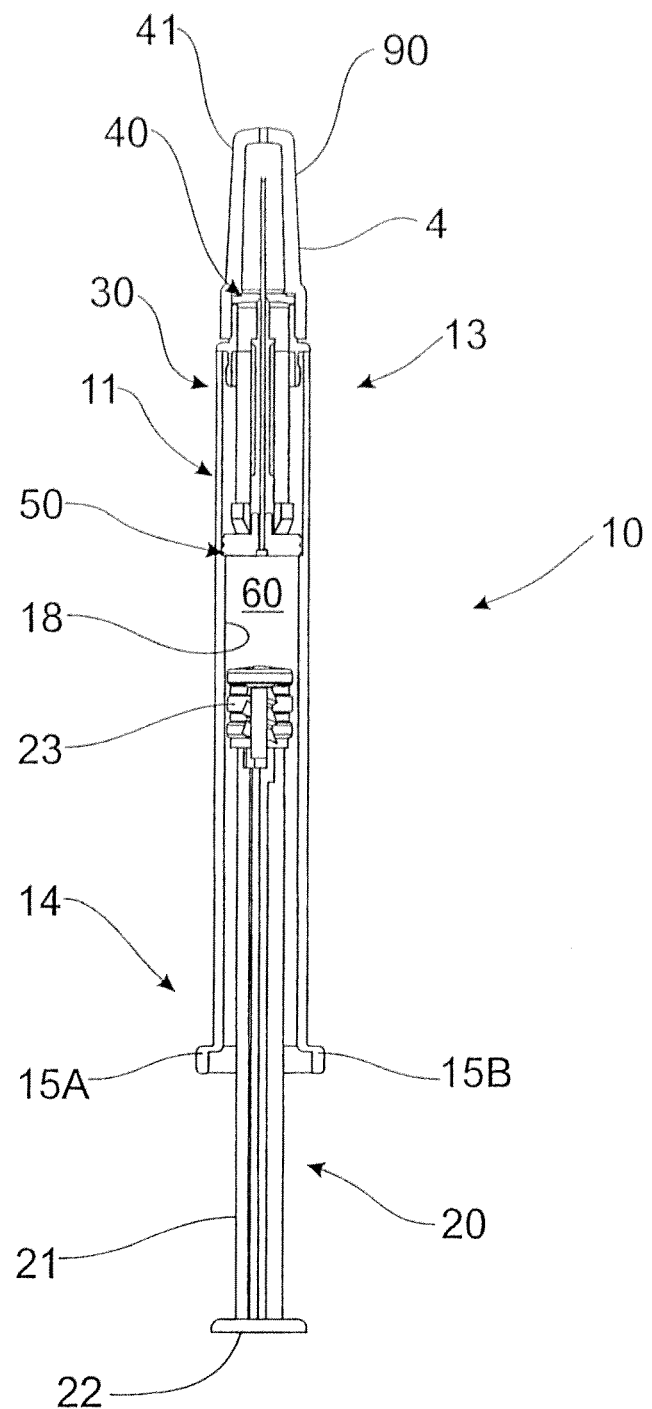
FIG. 1 is a side sectional view of a syringe having a needle sheath.

Referring to FIG. 1, syringe 10 comprises barrel 11, plunger 20, needle sheath 30, needle mount 40 and sheath seal 50. Barrel 11 comprises needle end 13 in which is located needle mount 40 comprising cannula 41. Protective cap 90 covers cannula 41 and is removed prior to use of syringe 10. Barrel 11 also comprises plunger end 14 at which are located paired finger grips 15A, 15B. Plunger seal 23, sheath seal 50 and inside wall 18 of barrel 11 define fluid space 60 inside barrel 11.

Figure 2:
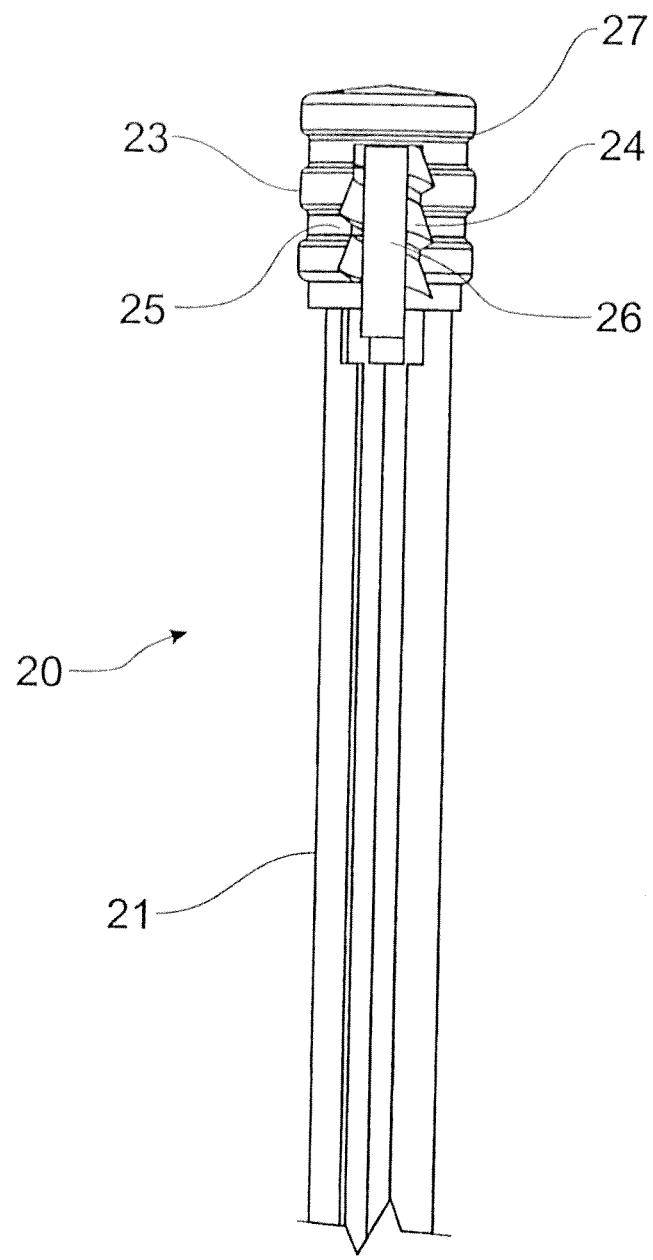
FIG. 2 is a side sectional view of a plunger.

Referring to FIG. 1 and FIG. 2, plunger 20 comprises plunger rod 21 and button 22 operable by a user to facilitate plunger 20 depression. Plunger 20 further comprises plunger seal 23 having ribbed sealing member 27, which is coupled to plunger rod 21 by way of coupling member 24 on plunger rod 21 engaging complementary recess 25 in plunger seal 23. Coupling member 24 comprises bore 26 to receive cannula 41 as hereinafter described.

In this particular embodiment, coupling member 24 and complementary recess 25 are screw-threadedly engaged.

Figure 3A:
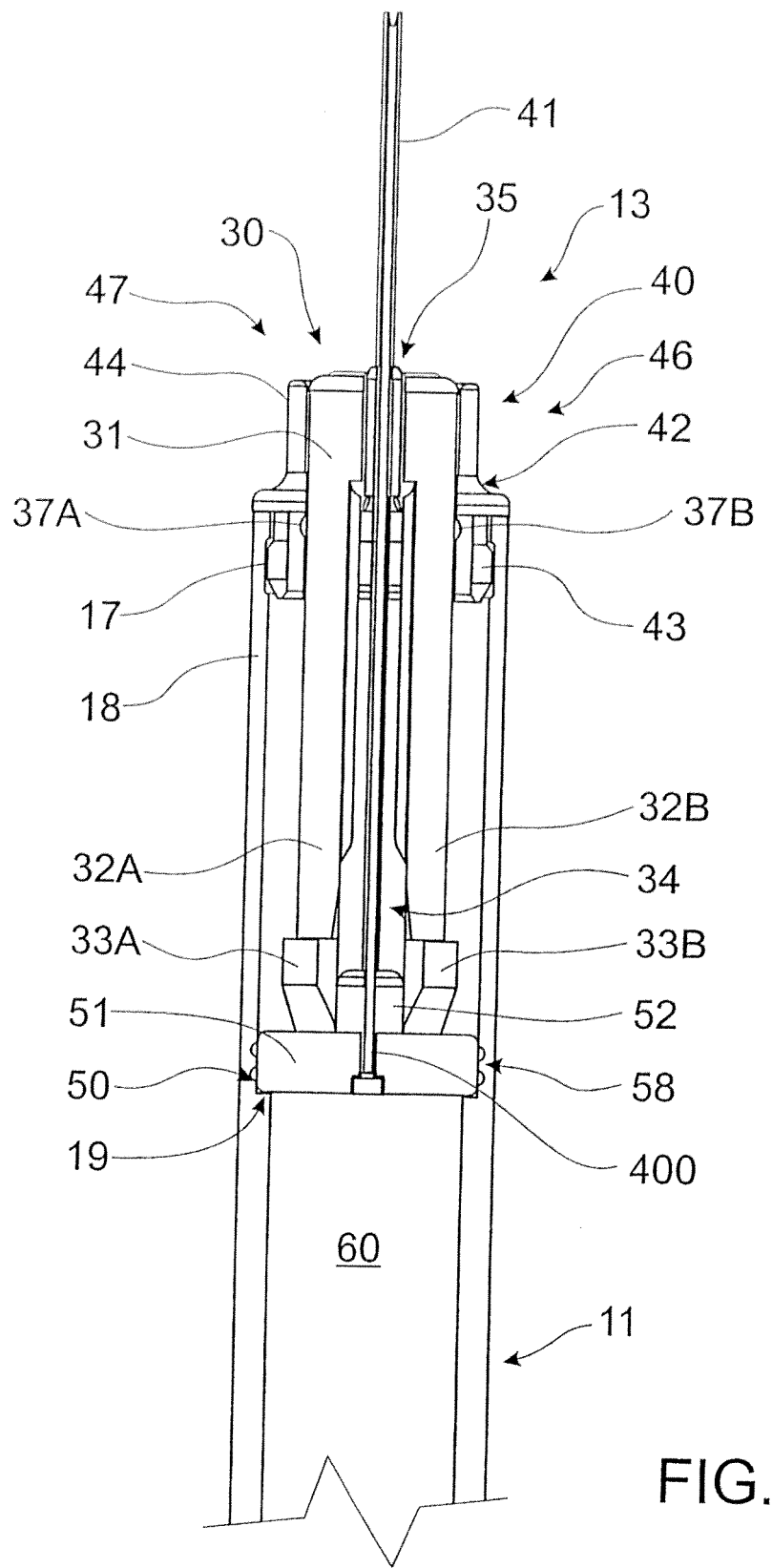
FIG. 3A is a side sectional view of a needle mount, needle sheath and sheath seal fitted into a syringe barrel
Figure 3B:
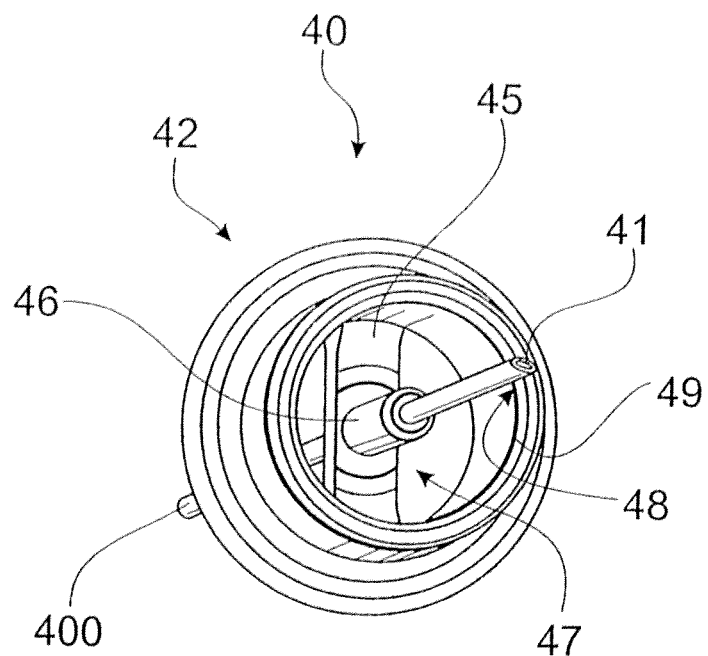
FIG. 3B is a perspective view of a needle mount.

Referring to FIG. 1 and FIGS. 3A and 3B needle sheath 30 comprises sheath body 31 having paired legs 32A, 32B that define groove 34 and cannula bore 35. Legs 32A, 32B respectively comprise stepped or barbed ends 33A, 33B.

Needle mount 40 is fitted at needle end 13 of barrel 11 through base 43 of needle mount body 42 being locatable within inner groove 17 of barrel 11. As best seen in FIG. 3B, needle mount body 42 further comprises cap 44 that comprises aperture 47, web 45 that supports boss 46 which in turn supports cannula 41, recess 48 and shoulder 49.

Needle sheath 30 is mounted into needle mount 40 so that legs 32A, 32B are located either side of web 45.

Sheath body 31 fits into aperture 47 to thereby co-operate with needle mount 40 to close needle end 13 of barrel 11. Notches 37A, 37B on sheath body 31 locate in recess 48 inside needle mount body 42 to hold needle sheath 30 in place. Sheath seal 50 is mounted inside barrel 11 and engages step 19, which prevents sheath seal 50 being refracted when plunger 20 is withdrawn to fill syringe 10. Sealing body 51 of sheath seal 50 abuts respective stepped ends 33A, 33B of legs 32A, 32B of sheath body 31 while boss 52 supports end 400 of cannula 41. Sealing member 58 of sheath seal 50 forms a fluid-tight tight seal with inside wall 18 of barrel 11.

Depression of plunger 20 expels fluid from fluid space through cannula 41.

Figure 4:
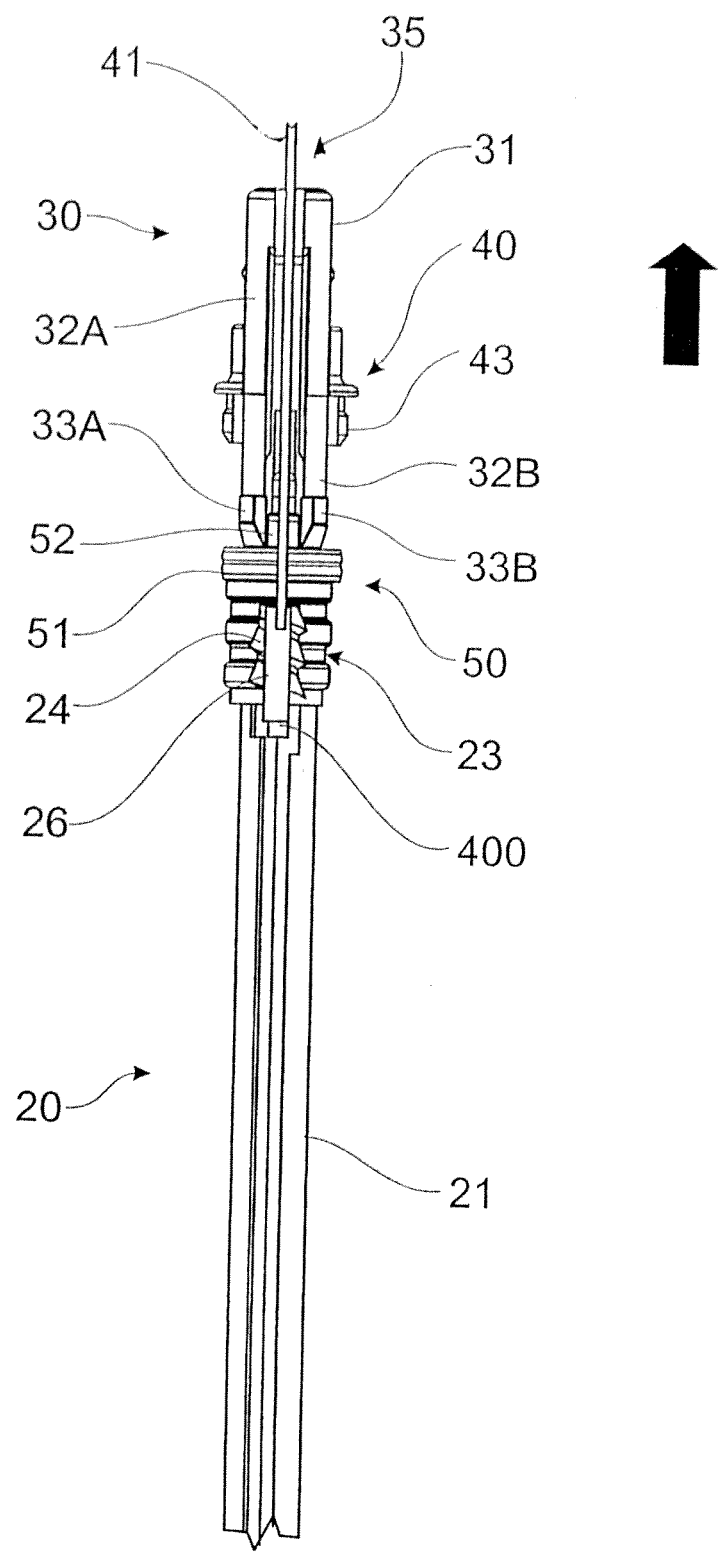
FIG. 4 is a side sectional view of a plunger, plunger seal, needle mount, needle sheath and sheath seal towards the end of plunger depression.

Referring to FIG. 4, towards the end of plunger 20 injection stroke, plunger seal 23 moves through fluid space 60, as indicated by the solid arrow, to eventually bear against sheath seal 50. As this occurs, cannula end 400 pierces plunger seal 23 and enters bore 26 in coupling member 24 of plunger 20 to thereby prevent any movement of cannula 41. Continued depression of plunger 20 and plunger seal 23 coupled thereto pushes sheath seal 50 against needle sheath 30 to move needle sheath further in the direction of needle end 13 of barrel 11 as indicated by the solid arrow.

Figure 5:
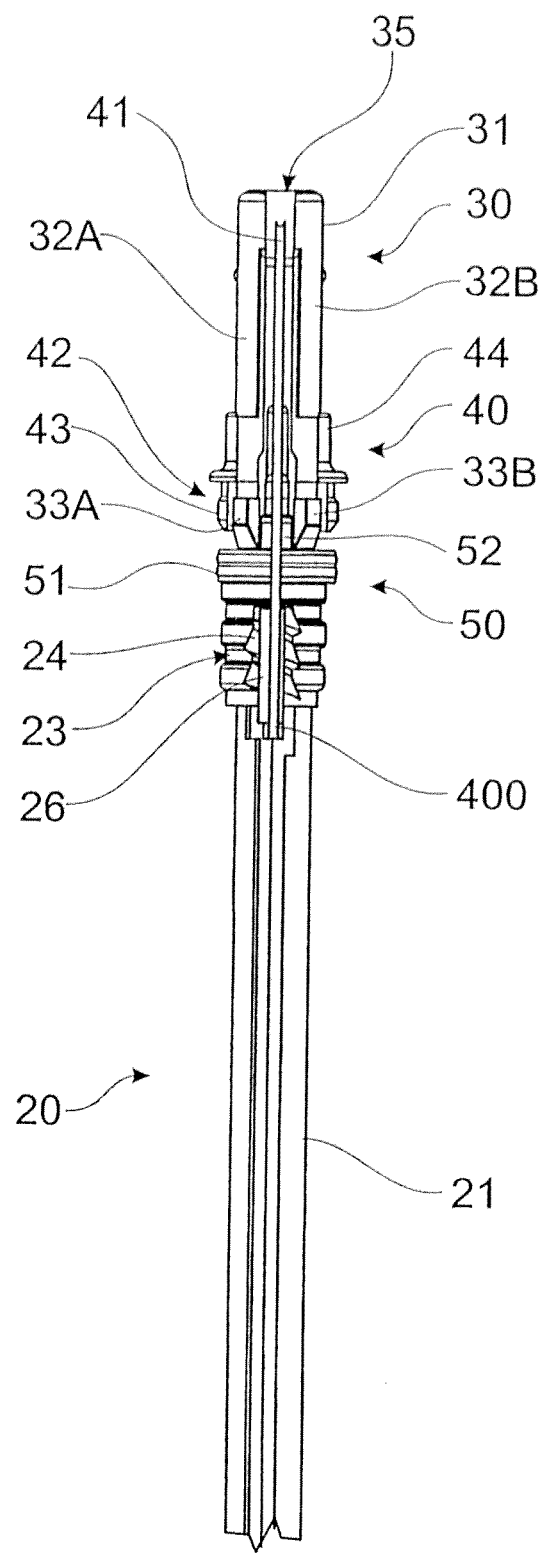
FIG. 5 is a side sectional view at the end of plunger depression wherein a needle sheath covers a cannula.
Figure 6:
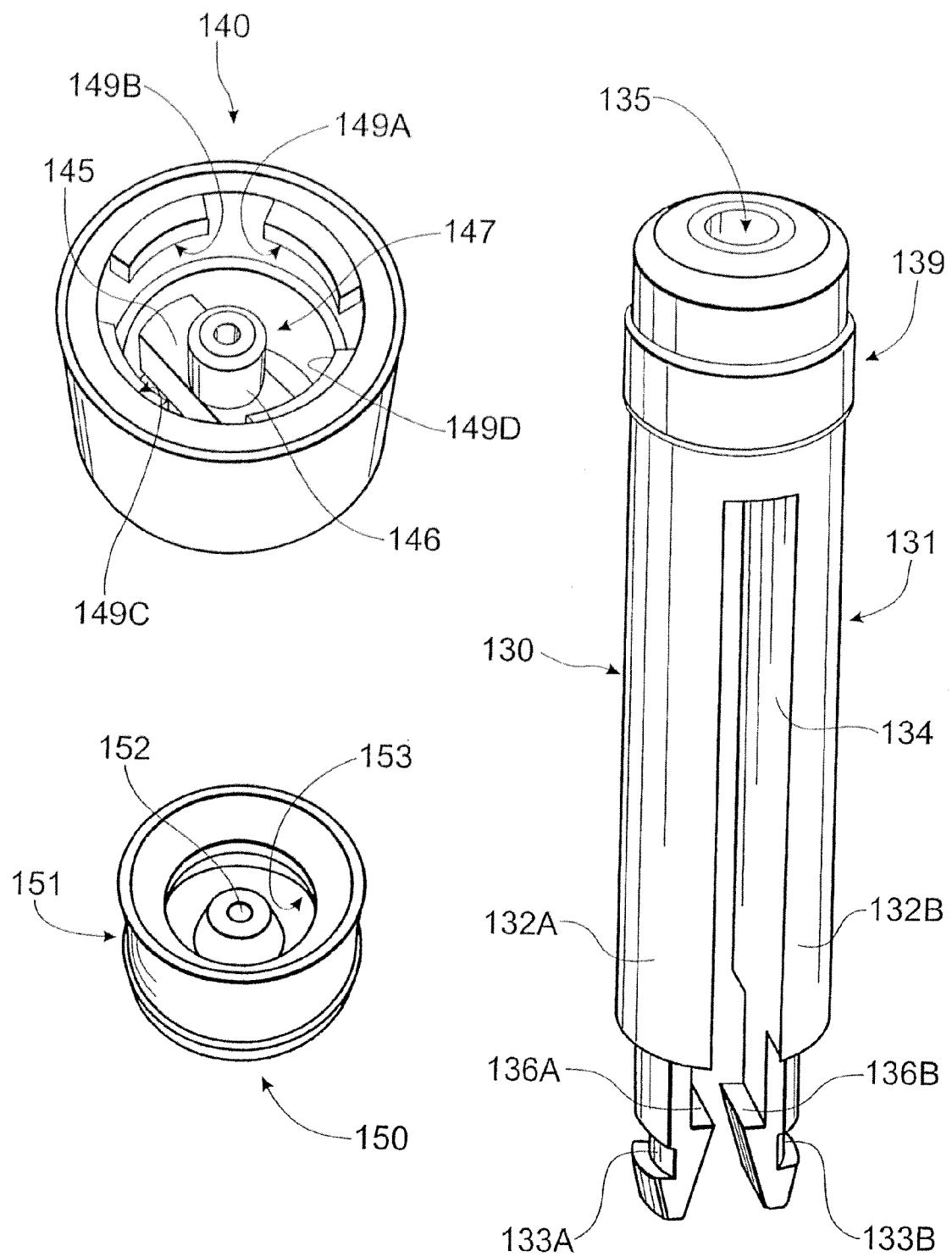
FIG. 6 shows a perspective view of components of another embodiment of a syringe having a needle sheath.
Figure 7:
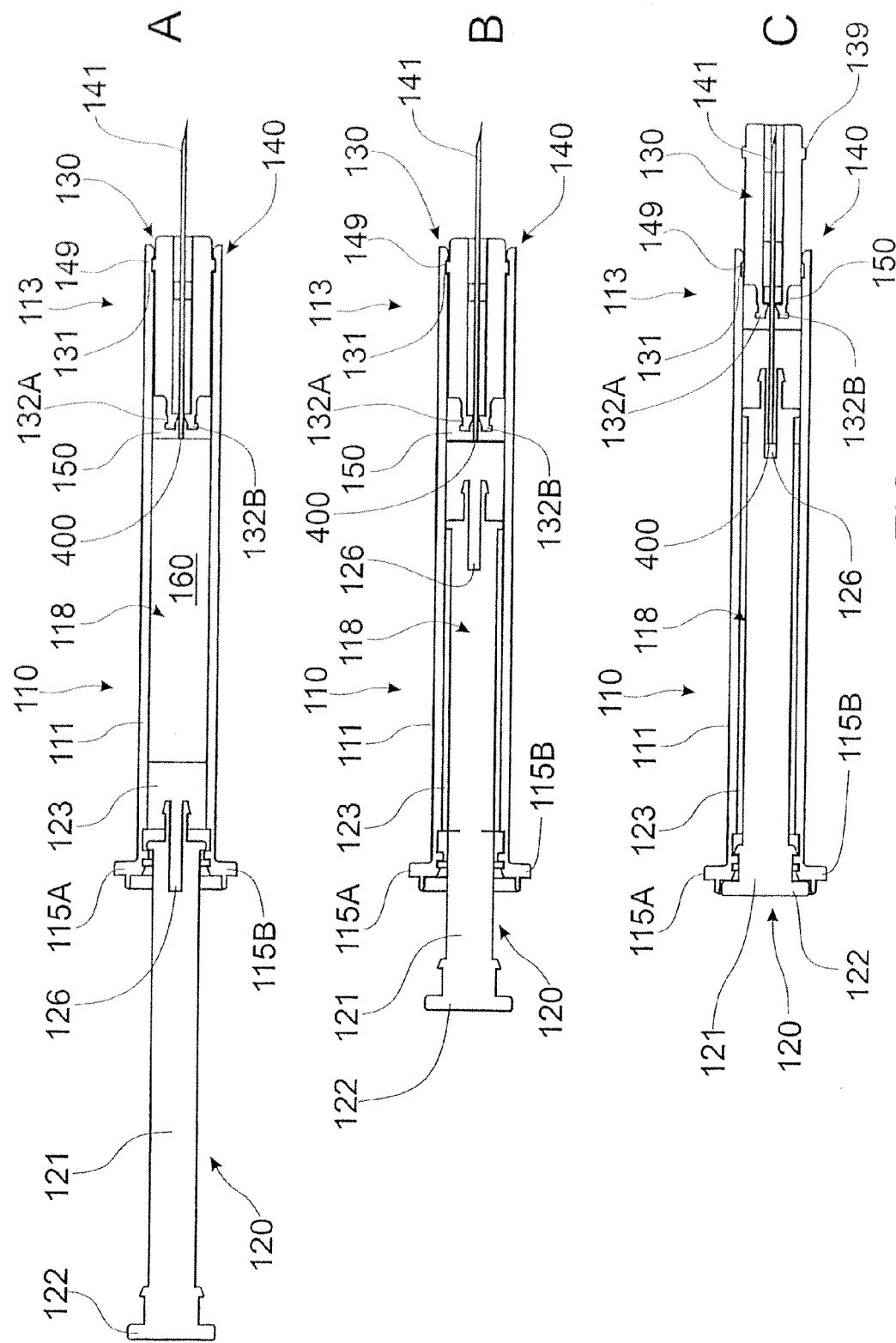
FIGS. 7A, 7B and 7C are respective sectional views of an embodiment of a prefilled syringe having a needle sheath showing the prefilled syringe before delivery (A), at the end of delivery (B) and after deployment of needle sheath (C)

When needle sheath 30 reaches shoulder 49 on the inside of needle mount body 42, cannula 41 is fully encapsulated by needle sheath 30, as shown in FIG. 5. Movement of needle sheath 30 will cease when stepped ends 33A, 33B of legs 32A, 32B clips into recess 48 in body 42 of needle mount 40.

Referring now to an alternative embodiment shown in FIG. 6 and FIG. 7A-C, syringe 110 comprises barrel 111 having finger grips 115A, 115B, plunger 120 having rod 121 and button 122, needle sheath 130, needle mount 140 and sheath seal 150. Note that in this embodiment, needle mount 140 is integral with needle end 113 of barrel 111, in contrast to the separate structure described in FIGS. 1-6.

Cannula 141 is located at needle end 113 of barrel 111, mounted via needle mount 140. Needle mount 140 further comprises aperture 147, web 145 that supports boss 146 which in turn supports cannula 141 and also comprises tabs 149A, 149B, 149C, 149D.

Needle sheath 130 is mounted into barrel 111 by way of ring 139 of sheath body 131 bearing against tabs 149A, B, C, D in inner wall of barrel 111. Sheath seal 150 comprises sealing body 151, support boss 152 and internal rim 153.

Sheath seal 150 is fitted to needle sheath 130 by way of barbed ends 133A, 133B of respective legs 132A, 132B engaging internal rim 153 of sheath seal 150. This prevents sheath seal 150 being drawn toward plunger end of barrel 111 during withdrawal of plunger 120 and filling of barrel 111.

Initially, plunger seal 123, sheath seal 150 and inner wall 118 of barrel 211 define fluid space 160.

Depression of plunger 120 expels fluid from fluid space 160 through cannula 141.

During plunger 120 depression, force applied to plunger 120 forces plunger seal 123 against sheath seal 150 which is coupled to needle sheath 130. Tabs 149A, B, C, D are shaped so that after a certain amount of force is applied by plunger 120 on sheath seal 150 at the end of injection, needle sheath 130 will release therefrom in needle end 113 of barrel 111 so that sheath seal 150 and needle sheath 130 will continue moving inside barrel 111 to thereby cover cannula 141. Groove 134 of needle sheath 130 surrounds web 145 and thereby allows needle sheath 130 to move relative thereto. Sheath seal 150 slides down cannula 141, support boss 152 allowing cannula 141 to pass therethrough, as it pushes needle sheath 130 down to cover cannula 141. Cannula 141 pierces plunger seal 123 and moves into bore 126 in plunger 120.

Movement of needle sheath 130 will cease when ledges 136A, 136B of legs 132A, 132B of needle sheath 130 bear against web 145 of needle mount 140.

Boss 146 provides lengthened support for cannula 141 and also allows for a larger cannula aperture 135 in needle sheath 130 to allow for easier assembly. Support boss 152 in sheath seal 150 accommodates and seals around end 400 of cannula 141 and sheath seal 150 seals needle end of barrel 111.

Reference is now made to FIGS. 8-13 which describe an embodiment of a spring-activated needle sheath.

Figure 8:
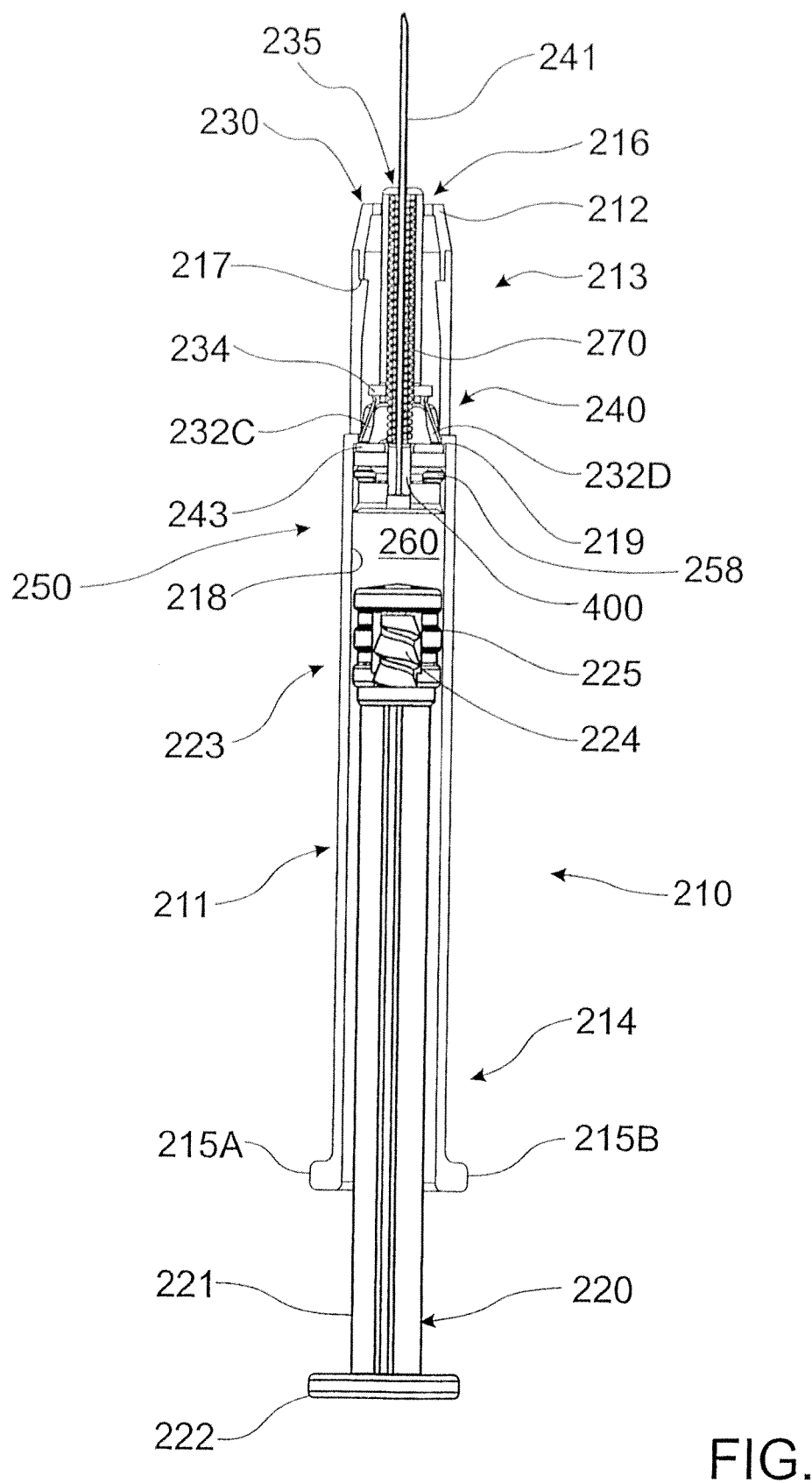
FIG. 8 is a side sectional view of a syringe having a spring-activated needle sheath.

Referring initially to FIG. 8, syringe 210 comprises barrel 211, plunger 220, needle sheath 230, needle mount 240, sheath seal 250 and spring 270. Barrel 211 comprises needle end 213 with sheath aperture 216 through which protrudes part of needle sheath 230 and cannula 241 mounted to needle mount 240. Sheath aperture 216 at needle end 213 of barrel 211 is bounded by rim 212. Barrel 211 also comprises circumferential step 219 and circumferential ledge 217 on inner wall 218. At plunger end 214 of barrel 211 are located paired finger grips 215A, 215B. Plunger seal 223, sheath seal 250 and inner wall 218 of barrel 211 define fluid space 260. Sealing member 258 of sheath seal 250 forms a fluid-tight tight seal with inside wall 218 of barrel 211.

Figure 9:
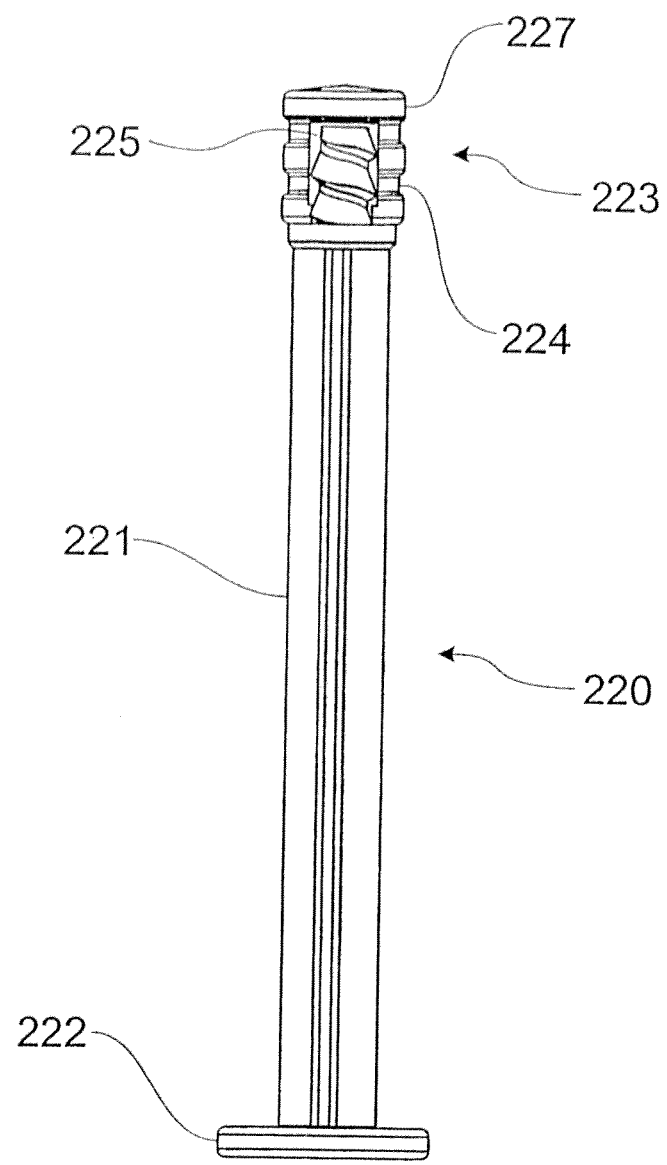
FIG. 9 is a side sectional view of a plunger.

Referring to FIG. 8 and FIG. 9, plunger 220 comprises plunger rod 221 and button 222 operable by a user to facilitate plunger 220 depression. Plunger 220 further comprises plunger seal 223 having ribbed sealing member 227, which is coupled to plunger rod 221 by way of screw coupling member 224 on plunger rod 221 engaging complementary, threaded recess 225 in plunger seal 223.

Figure 10:
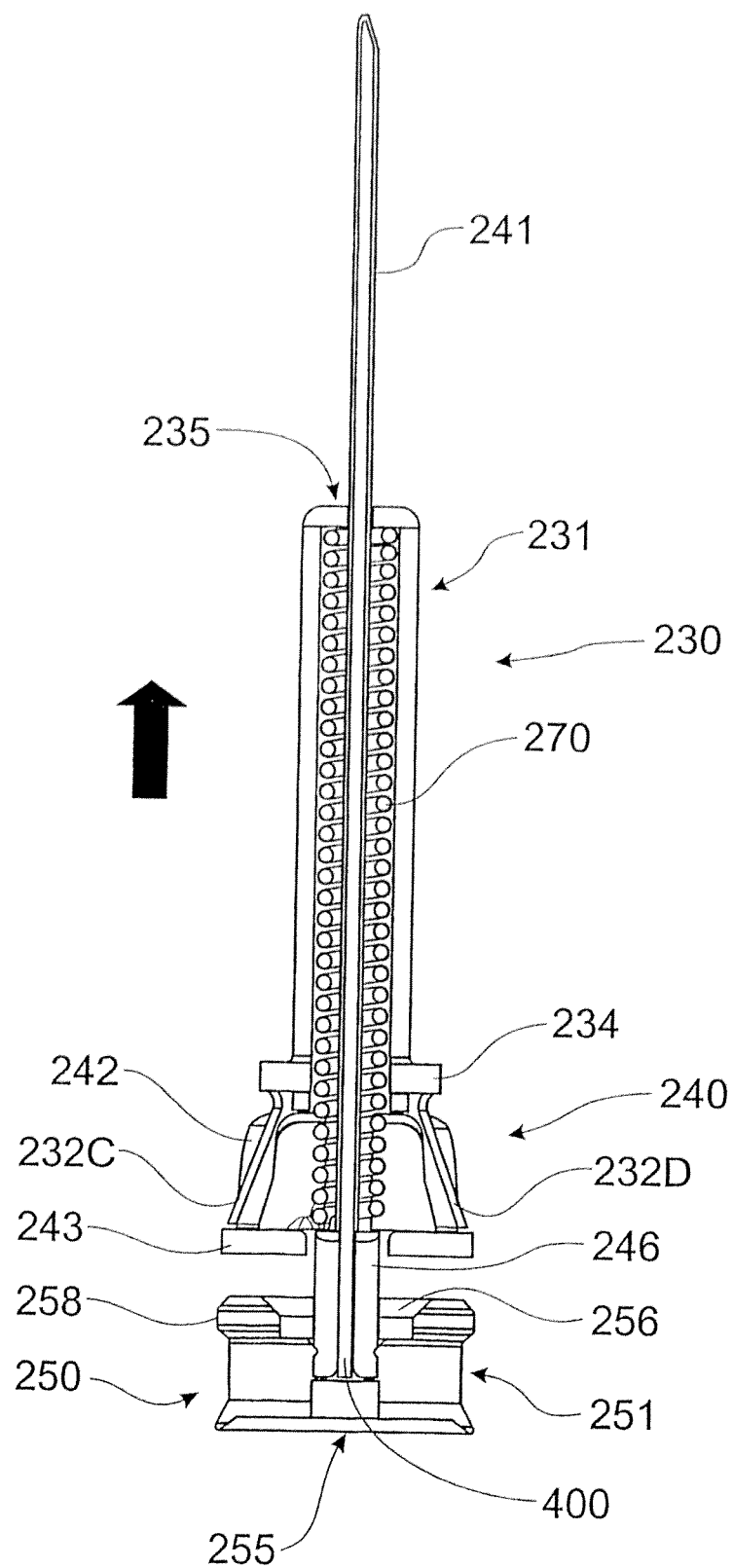
FIG. 10 is a side sectional view of a needle mount, needle sheath with spring and sheath seal fitted into a syringe barrel.
Figure 11:
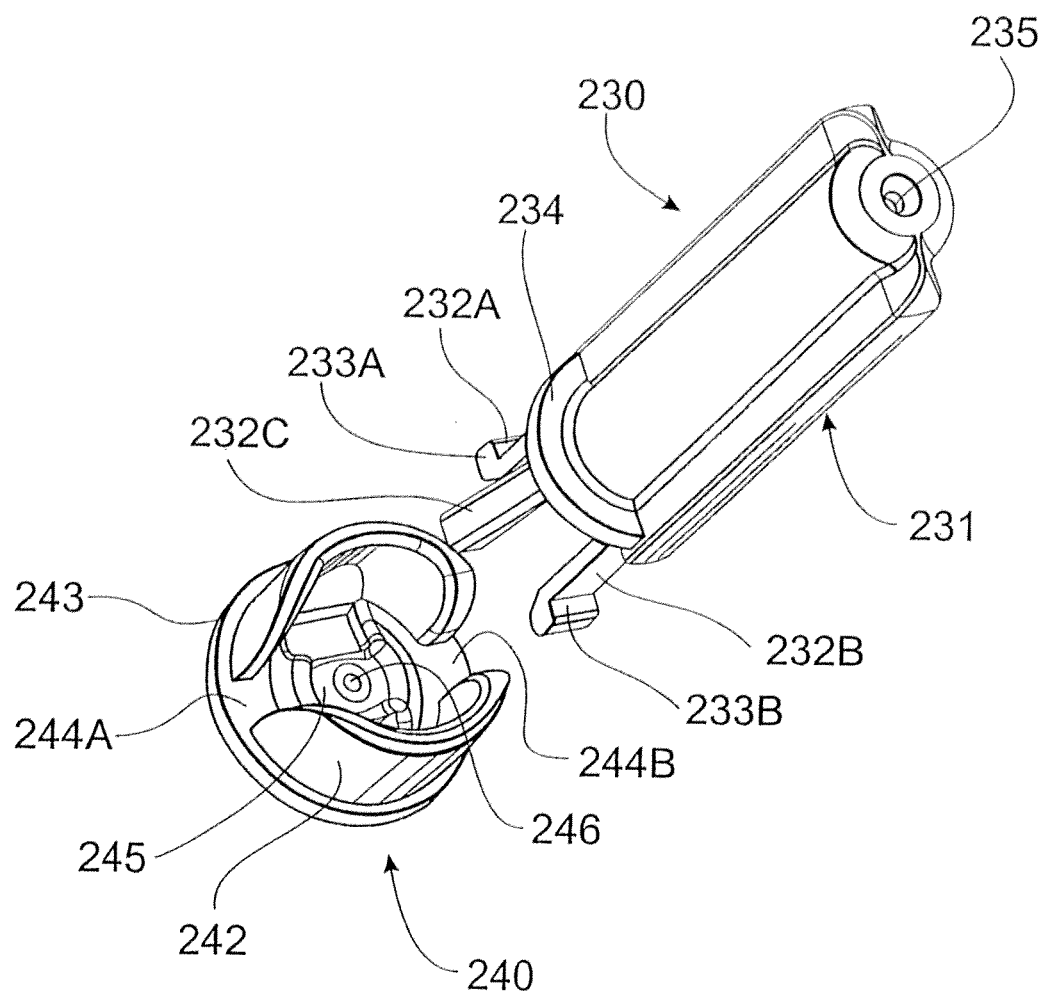
FIG. 11 is a perspective view of a needle mount and needle sheath.

Referring to FIG. 10 and FIG. 11, needle sheath 230 comprises sheath body 231 having cannula bore 235, ledge 234 and legs 232A, 232B, 232C, 232D. Legs 232C, 232D are relatively splayed compared to legs 232A, 232B which respectively terminate in stepped ends 233A, 233B.

Needle mount 240 is a separate structure as in FIGS. 1-6 and comprises body 242 having base 243 and cutaways 244A, 244B and web 245 that supports elongate boss 246 which in turn supports cannula 241.

Needle mount 240 is fitted at needle end 213 of barrel 211 either by adhesive or an interference fit between base 243 and circumferential step 219 on inside wall 218 of barrel 211, which prevents needle mount 240 traveling further toward needle end 213 of barrel 211. Spring 270 is fitted over cannula 241 and needle sheath 230 is placed over cannula 241 and forced towards needle mount 240, thereby compressing spring 270. Needle sheath 230 is mounted into needle mount 240 so that legs 232A, 232B are located either side of web 245 and elongate boss 246, stepped ends 233A, 233B clipping under base 243 of needle mount body 242.

Splayed legs 232C, 232D are angularly disposed through cutaways 244A, 244B and terminate against base 243 of needle mount body 242.

End 400 of cannula 241 extends through cannula bore 235 of needle sheath 230 and elongate boss 246 to communicate with fluid space 260 in barrel 211.

Sheath seal 250 comprises sealing body 251, aperture 255 and seat 256, which in this embodiment has a recessed taper. Sheath seal 250 is coupled to needle mount 240 by way of elongate boss 246 fitting into aperture 255. Cannula 241 extends through cannula bore 235 of needle sheath 230 and elongate boss 246 of needle mount 240 to communicate with fluid space 260 in barrel 211, although without extending beyond central aperture 255 of sheath seal 250.

Initially, plunger seal 223 and sheath seal 250 define fluid space 260 inside barrel 211.

Depression of plunger 220 expels fluid from fluid space 260 through cannula 241.

Towards the end of plunger 220 injection stroke to deliver fluid contents of syringe 210, plunger seal 223 engages sheath seal 250 thereby moving sheath seal 250 in the direction indicated by the solid arrow shown in FIG. 10. Seat 256 of sheath seal 250 engages respective stepped ends 233A, 233B of legs 232A, 232B of needle sheath 230, forcing them radially inwards, thereby releasing needle sheath 230 which was held in place under spring 270 bias.

Figure 12:
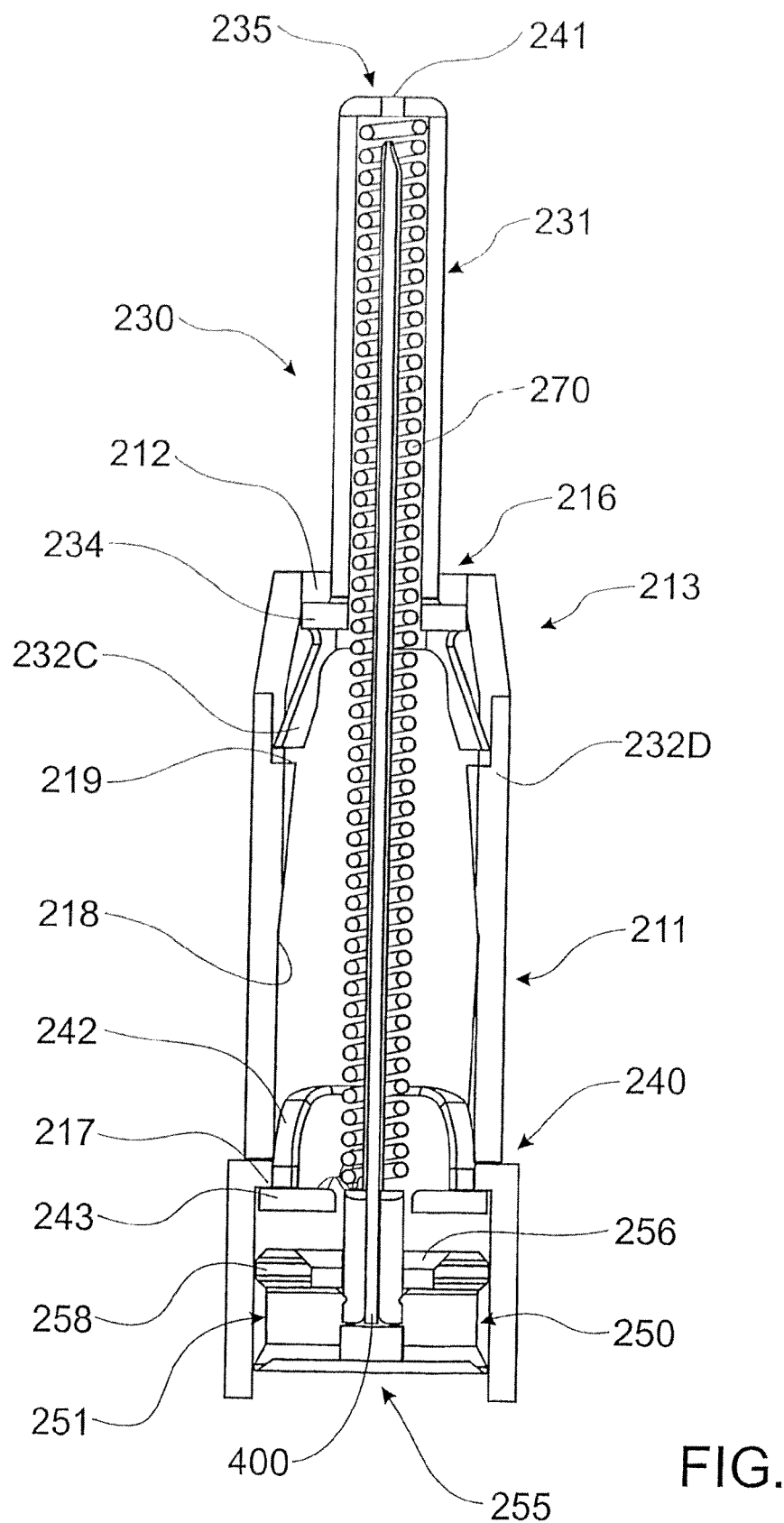
FIG. 12 is a side sectional view at the end of plunger depression wherein a spring-activated needle sheath covers a cannula.

Decompression of spring 270 drives needle sheath 230 in the direction of needle end 213 of barrel 211 as indicated by the solid arrow, so that cannula 241 is fully encapsulated by needle sheath 230, as shown in FIG. 12. Sheath 230 cannot travel beyond needle end 213 of barrel 211 or be removed from barrel 211 because ledge 234 bears against rim 212 that bounds sheath aperture 216.

When needle sheath 230 encapsulates cannula 241, splayed legs 232C, 232D of needle sheath 230 clip out over circumferential ledge 219 on inside wall 218 of barrel 211 thereby preventing sheath from being pushed back into the barrel, and exposing the needle.

The syringe 10 of the present invention may be a pre-filled syringe or may be a syringe where fluid is drawn into barrel 11 by a user.

Figure 13:
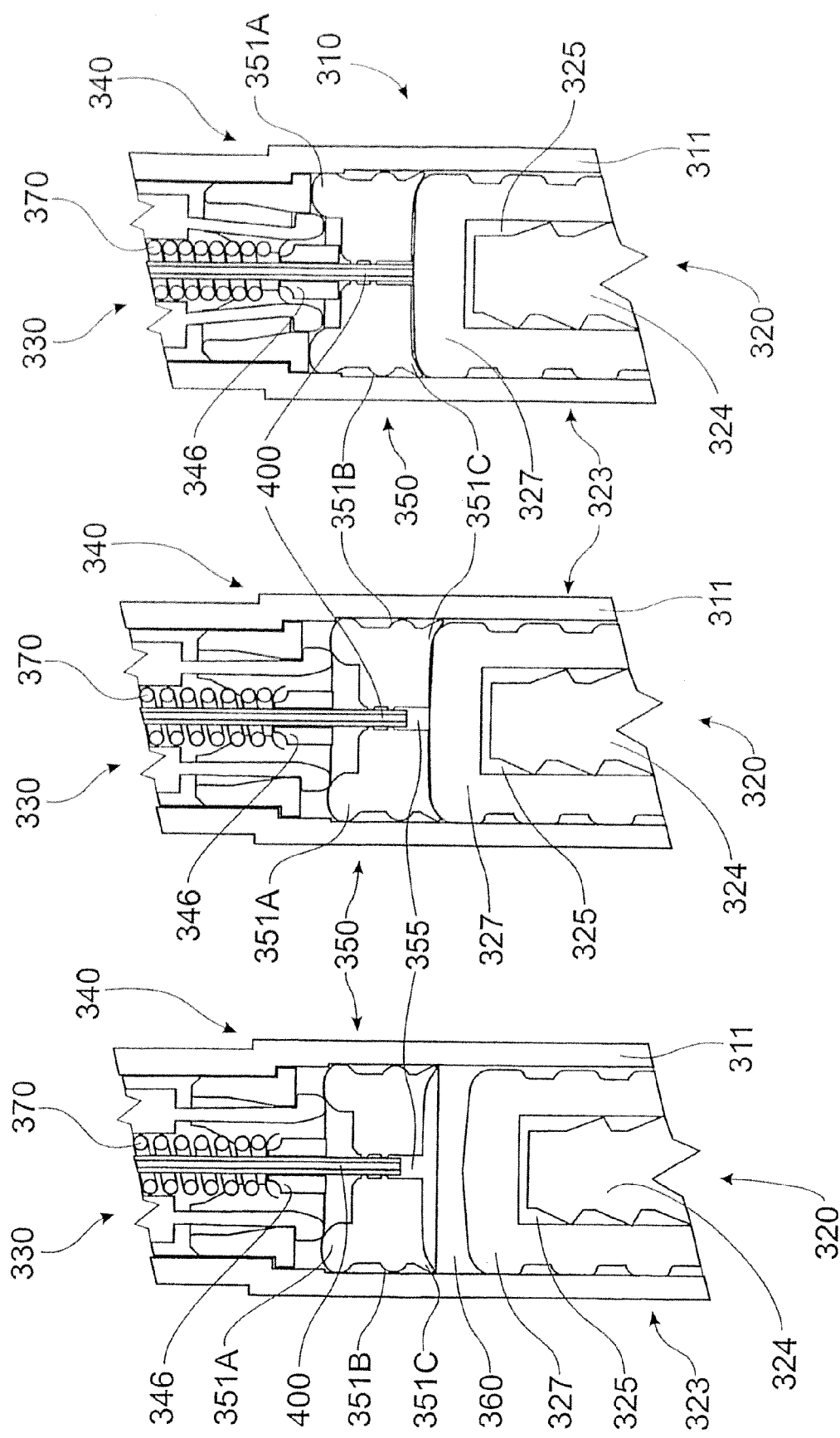
FIG. 13 is a side sectional view of an alternative embodiment of a sheath seal.

One particular variation contemplated by the present invention is described with reference to FIG. 13, which variation is particularly relevant to a prefilled syringe 310. Sheath seal 350 comprises sealing members 358A, 358B and 358C and directly seals cannula end 400 to avoid contact between boss 346 and fluid space 360. In this regard, boss 346 is relatively shorter than elongate boss 346 previously described, to thereby allow aperture 355 of sheath seal 350 to directly seal onto cannula end 400 and thereby allow movement of sheath seal 350 along cannula 341 until sheath seal 350 engages needle sheath 330 as plunger 320 is depressed (shown progressively, left to right, in FIG. 13).

Figure 14A:
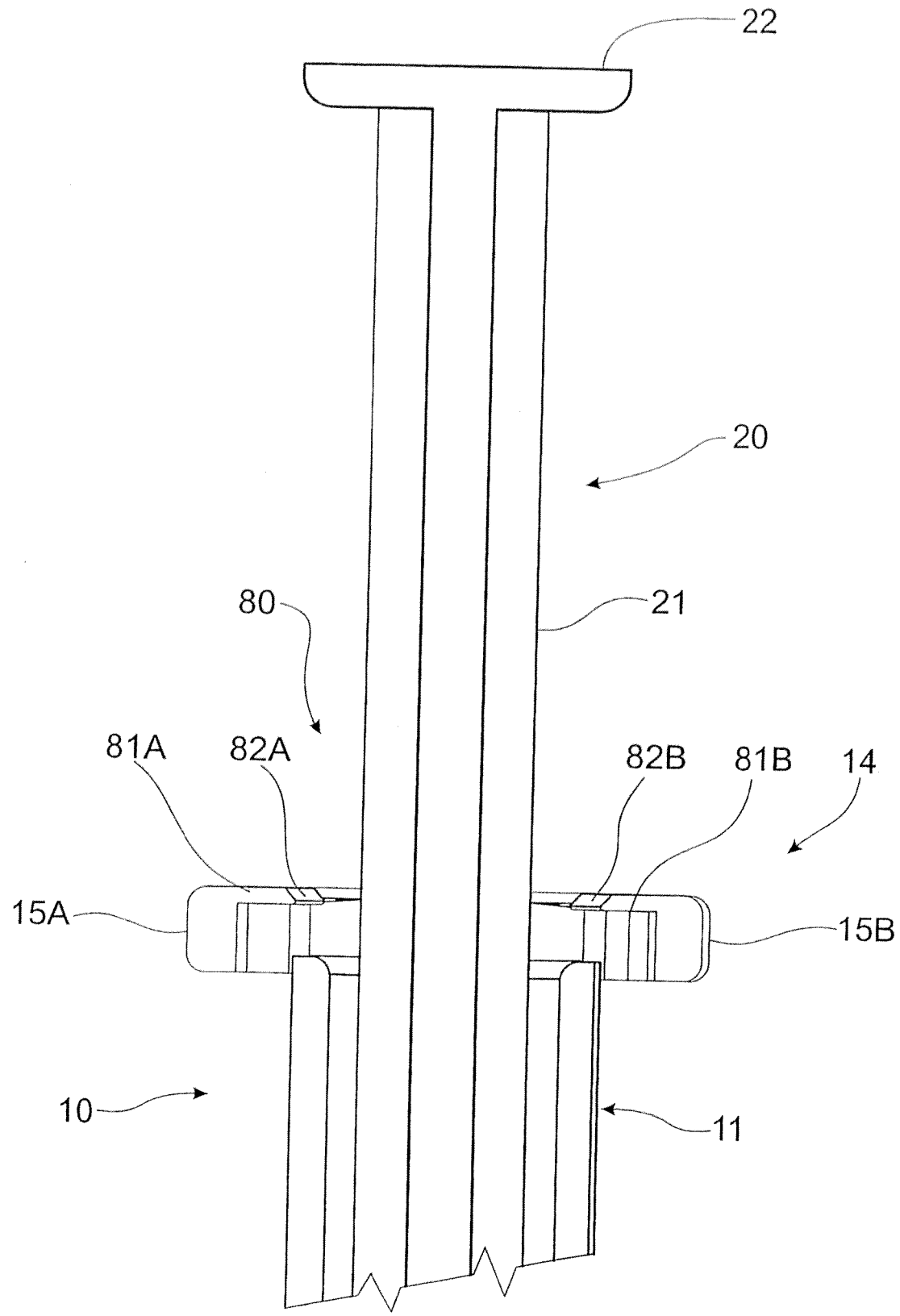
FIG. 14A is a side sectional view of a syringe comprising a plunger disabling means before plunger depression and FIG. 14B is a side sectional view of syringe comprising a plunger disabling means after plunger depression.
Figure 14B:
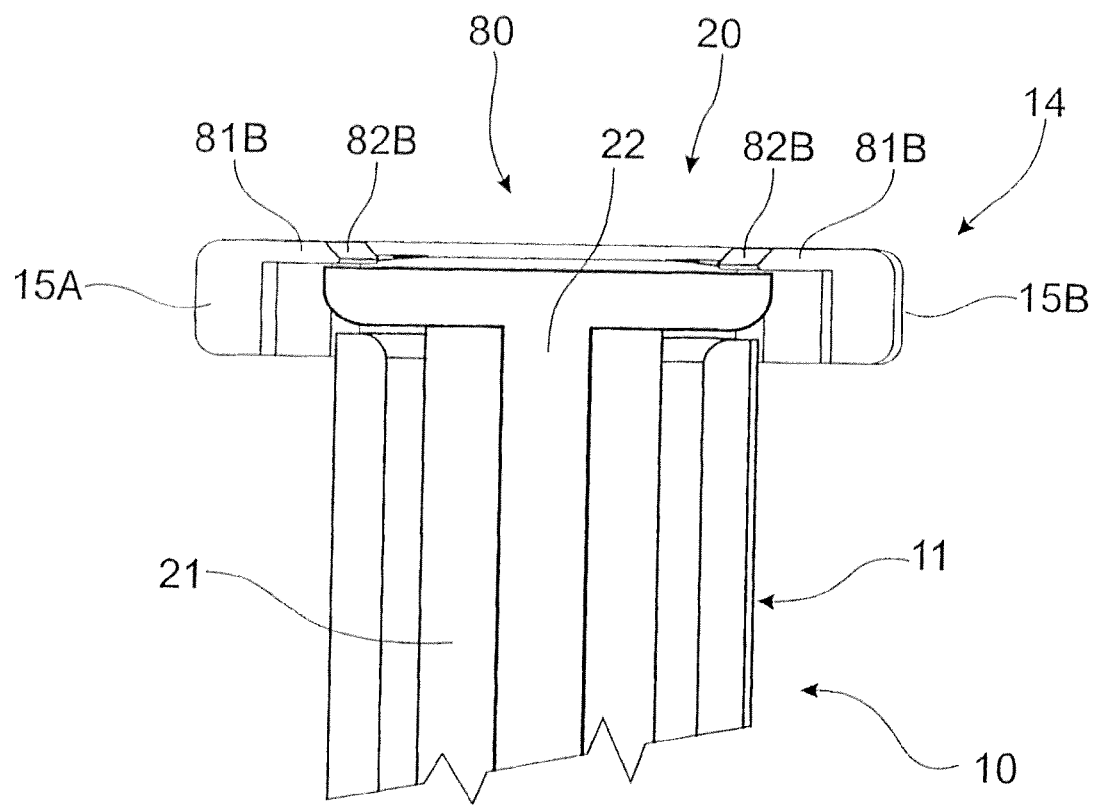

The invention also contemplates incorporation of a plunger disabling means 80 that may be applicable to any of the aforementioned embodiments of syringe 10. An embodiment of a plunger disabling means 80 is shown in FIG. 14A where plunger end 14 of barrel 11 comprises opposed ledges 81A, 81B, respectively having tapered surfaces 82A, 82B which allow travel of button 22 of plunger 20 past ledges 81A, 81B toward needle end 13 of barrel 11 at the end of plunger 20 depression so that button 22 clips under ledges 81A, 81B, thereby to impede, prevent or otherwise hinder subsequent withdrawal of plunger 20, as shown in FIG. 14B. This assists in maintaining sheath 30 in its covering position over cannula 41 and prevents a user pushing sheath 30 back into barrel 11 in an attempt to re-use syringe 10.

Alternatively, the invention also contemplates incorporation of a plunger disabling means such as according to an embodiment described in International Application PCT/AU2005/000106, which is herein incorporated by reference in its entirety.

In this particular embodiment, the plunger comprises two opposed ratchets that are respectively alignable with the two pawls so as to be capable of engagement by the pawls and thereby impede, prevent or otherwise hinder withdrawal of the plunger during or following depression of the plunger. The barrel further comprises a collar having an inner member and an outer member that are incapable of rotation relative to each other. The outer member comprises the two pawls and further comprises two fingers that respectively slidably engage opposed guide slots on the plunger to thereby prevent or minimize rotation of the plunger relative to the collar. The inner member of the collar is operable to prevent engagement of the plunger ratchet by the two pawls until the plunger is depressed.

According to these embodiments, utilization of plunger disabling means 80 allows plunger 20 to be immovably disabled at the end of depression and fluid delivery thereby maintaining boss 52 of sheath seal 50 in a position between legs 32A, 32B that prevents legs 32A, 32B of needle sheath 30 being "squeezed" together and needle sheath 30 removed from needle end 13 of barrel 11.

In light of the foregoing it will be appreciated that the present invention provides a needle sheath manually activated by plunger depression or, optionally, a spring, which prevents, minimizes or reduces the risk of needlestick injury and/or syringe re-use.

A particular feature of the syringe needle sheath described herein is that it is relatively simple in structure and does not require a guiding member to assist guided movement of the sheath over the needle or to positively retain the sheath in its protection position over the needle.

A particular advantage of the spring activated syringe needle sheath described herein is that the spring is pre-compressed, rather than gradually compressed during plunger depression, which provides a more acceptable "feel" to the syringe user and hence improves the commercial attractiveness of the syringe.

Optionally, a further advantage is that a plunger disabling means may be included with the syringe of the invention to at least minimize the probability of re-use.

Throughout the specification, the aim has been to describe the preferred embodiments of the invention without limiting the invention to any one embodiment or specific collection of features. Various changes and modifications may be made to the embodiments described and illustrated without departing from the present invention.

All patent literature referred to in this specification is incorporated herein by reference in its entirety.

What is claimed is:

1. A syringe comprising a barrel, a needle and a needle mount fitted to the barrel to prevent movement of the needle and needle mount relative to the barrel, a plunger, a needle sheath slidably located within the barrel, an initially compressed spring and a sheath seal that comprises an aperture, wherein said needle mount comprises an elongated boss fitted into said aperture to thereby couple the sheath seal and the needle mount, wherein an end of said needle is supported by and extends through the entirety of said elongate boss such that the end of said needle terminates at an end of said elongated boss in fluid communication with a fluid space in said barrel, arranged so that depression of said plunger urges said sheath seal to bear against said needle sheath and thereby release said needle sheath from said needle mount to facilitate decompression of said spring and thereby move said needle sheath to cover or at least partly enclose the needle after expelling fluid contents from the syringe.

2. The syringe of claim 1, wherein said needle sheath co-operates with said needle mount to initially compress said spring until said needle sheath is released from said needle mount to facilitate decompression of said spring.

3. The syringe of claim 2, wherein the needle sheath comprises legs that engage said needle mount to facilitate initial compression of the spring until said needle sheath is released from said needle mount to facilitate decompression of said spring.

4. The syringe of claim 1, wherein the sheath seal comprises an aperture and said needle mount comprises a boss, wherein an end of said needle extends into said aperture in fluid communication with the fluid space in said barrel.

5. The syringe of claim 1, further comprising a plunger seal that engages said sheath seal and urges said sheath seal to bear against said needle sheath.

6. The syringe of claim 1, further comprising a plunger disabling means operable to impede, prevent or otherwise hinder withdrawal of the plunger during depression of the plunger or after depression of the plunger is complete.

7. The syringe of claim 1, which is a pre-filled syringe.

* * * * *